(12) United States Patent
Remez et al.

(10) Patent No.: US 9,671,304 B2
(45) Date of Patent: *Jun. 6, 2017

(54) METHODS AND SYSTEMS FOR THE MANUFACTURE AND INITIATION OF A PRESSURE DETECTION MAT

(75) Inventors: Tal Natan Remez, Jerusalem (IL); Amir Ben Shalom, Modiin (IL); Gusti Yoram Averbuch, Modiin (IL)

(73) Assignee: Enhanced Surface Dynamics, Inc., Wellesley, MA (US)

(*) Notice: Subject to any disclaimer, the term of this patent is extended or adjusted under 35 U.S.C. 154(b) by 481 days.

This patent is subject to a terminal disclaimer.

(21) Appl. No.: 14/232,366

(22) PCT Filed: Jul. 11, 2012

(86) PCT No.: PCT/IB2012/053538
§ 371 (c)(1),
(2), (4) Date: Apr. 15, 2014

(87) PCT Pub. No.: WO2013/008187
PCT Pub. Date: Jan. 17, 2013

(65) Prior Publication Data
US 2014/0373594 A1 Dec. 25, 2014

Related U.S. Application Data

(60) Provisional application No. 61/507,418, filed on Jul. 13, 2011.

(51) Int. Cl.
*G01L 25/00* (2006.01)
*G01L 1/14* (2006.01)
(Continued)

(52) U.S. Cl.
CPC ............ *G01L 25/00* (2013.01); *A61B 5/6892* (2013.01); *G01B 7/16* (2013.01); *G01L 1/142* (2013.01);
(Continued)

(58) Field of Classification Search
CPC .......... G01L 25/00; G01L 1/146; G01L 1/205; G01L 1/142; G01L 1/22; A61B 5/6892;
(Continued)

(56) References Cited

U.S. PATENT DOCUMENTS

| 4,503,286 | A | | 3/1985 | Kubo et al. | |
|---|---|---|---|---|---|
| 4,526,043 | A | * | 7/1985 | Boie ..................... | G01B 7/004 361/283.3 |

(Continued)

FOREIGN PATENT DOCUMENTS

| CN | 101109769 A | 1/2008 |
|---|---|---|
| DE | 3227550 | 1/1983 |

(Continued)

OTHER PUBLICATIONS

European Patent Office, Extended Search Report for the corresponding European Patent Application No. 12810788.5 mailed Feb. 2, 2015.

(Continued)

*Primary Examiner* — Hezron E Williams
*Assistant Examiner* — Marrit Eyassu
(74) *Attorney, Agent, or Firm* — Brooks Kushman P.C.

(57) ABSTRACT

A method for manufacture of a pressure sensing mat comprising the steps of: (a) preparing two conductive layers, each conductive layer comprising an array of conducting strips mounted upon a substrate arranged in a parallel fashion, wherein the conducting strips of the first conductive layer are oriented perpendicularly in relation to the conducting strips of the second conductive layer; (b) for each conductive layer, connecting each of the conducting strips to a communication line; (c) sandwiching a compressible layer between the two conductive layers; and (d) performing a pressure reading standardization test to the mat.

19 Claims, 11 Drawing Sheets

(51) Int. Cl.
  *G01L 1/20* (2006.01)
  *A61B 5/00* (2006.01)
  *G01B 7/16* (2006.01)
  *G01L 1/22* (2006.01)

(52) U.S. Cl.
  CPC .............. *G01L 1/146* (2013.01); *G01L 1/205* (2013.01); *G01L 1/22* (2013.01); *A61B 2562/0247* (2013.01); *A61B 2562/046* (2013.01); *Y10T 29/49004* (2015.01)

(58) Field of Classification Search
  CPC ...... A61B 2562/0247; A61B 2562/046; G01B 7/16; Y10T 29/49004
  USPC ................ 73/1.08, 862.046; 29/593; 901/46; 361/283.3
  See application file for complete search history.

(56) References Cited

U.S. PATENT DOCUMENTS

| | | | |
|---|---|---|---|
| 4,554,930 A | 11/1985 | Kress | |
| 4,758,815 A | 7/1988 | Lovell | |
| 4,795,998 A | 1/1989 | Dunber et al. | |
| 4,827,763 A * | 5/1989 | Bourland | A61B 5/6892 361/283.1 |
| 4,929,803 A | 5/1990 | Yoshida et al. | |
| 5,010,772 A | 4/1991 | Bourland et al. | |
| 5,030,508 A | 7/1991 | Kuhn et al. | |
| 5,033,291 A | 7/1991 | Podoloff et al. | |
| 5,086,652 A | 2/1992 | Kropp | |
| 5,102,727 A | 4/1992 | Pittman et al. | |
| 5,131,259 A | 7/1992 | Kropp | |
| 5,162,135 A | 11/1992 | Gregory et al. | |
| 5,276,432 A | 1/1994 | Travis | |
| 5,505,072 A | 4/1996 | Oreper | |
| 5,571,973 A | 11/1996 | Taylot | |
| 5,642,096 A | 6/1997 | Leyerer et al. | |
| 5,656,785 A * | 8/1997 | Trainor | A61F 2/4657 73/862 |
| 5,720,892 A | 2/1998 | DeAngelis et al. | |
| 5,756,904 A | 5/1998 | Oreper et al. | |
| 5,808,552 A | 9/1998 | Wiley et al. | |
| 5,856,644 A * | 1/1999 | Burgess | H01H 1/029 200/61.43 |
| 5,905,209 A | 5/1999 | Oreper | |
| 5,942,733 A | 8/1999 | Allen et al. | |
| 5,970,789 A | 10/1999 | Meyer et al. | |
| 5,993,400 A | 11/1999 | Rincoe et al. | |
| 6,014,346 A | 1/2000 | Malone | |
| 6,032,542 A | 3/2000 | Warnick et al. | |
| 6,067,019 A | 5/2000 | Scott | |
| 6,155,120 A | 12/2000 | Taylor | |
| 6,216,545 B1 | 4/2001 | Taylor | |
| 6,216,546 B1 | 4/2001 | Bahr | |
| 6,225,814 B1 | 5/2001 | Oreper et al. | |
| 6,244,272 B1 | 6/2001 | Montant et al. | |
| 6,287,253 B1 | 9/2001 | Ortega et al. | |
| 6,367,106 B1 | 4/2002 | Gronsman | |
| 6,386,051 B1 | 5/2002 | Yoshimi et al. | |
| 6,417,777 B2 | 7/2002 | Fitzgerald et al. | |
| 6,432,737 B1 | 8/2002 | Webster | |
| 6,438,776 B2 | 8/2002 | Ferrand et al. | |
| 6,441,742 B1 | 8/2002 | Lovely et al. | |
| 6,543,299 B2 | 4/2003 | Taylor | |
| 6,546,813 B2 | 4/2003 | Hubbard, Jr. | |
| 6,721,980 B1 | 4/2004 | Price et al. | |
| 6,897,781 B2 | 5/2005 | Cooper et al. | |
| 6,945,115 B1 | 9/2005 | Wang | |
| 6,964,205 B2 | 11/2005 | Papakostas et al. | |
| 6,987,232 B2 | 1/2006 | Smith et al. | |
| 6,993,954 B1 | 2/2006 | George et al. | |
| 7,030,764 B2 | 4/2006 | Smith et al. | |
| 7,090,647 B2 | 8/2006 | Mimura et al. | |
| 7,119,696 B2 | 10/2006 | Borugian | |
| 7,201,063 B2 | 4/2007 | Taylor | |
| 7,258,026 B2 | 8/2007 | Papakostas et al. | |
| 7,304,580 B2 | 12/2007 | Sullivan et al. | |
| 7,319,386 B2 | 1/2008 | Collins, Jr. et al. | |
| 7,330,127 B2 | 2/2008 | Price et al. | |
| 7,377,133 B2 | 5/2008 | Sandbach et al. | |
| 7,378,975 B1 | 5/2008 | Smith et al. | |
| 7,464,605 B2 | 12/2008 | Douglas et al. | |
| 7,480,951 B2 | 1/2009 | Weismiller et al. | |
| 7,531,203 B2 | 5/2009 | Tao et al. | |
| 7,557,718 B2 | 7/2009 | Petrosenko et al. | |
| 7,559,106 B1 | 7/2009 | Crousore et al. | |
| 7,568,246 B2 | 8/2009 | Weismiller et al. | |
| 7,591,165 B2 | 9/2009 | Papakostas et al. | |
| 7,629,890 B2 | 12/2009 | Sullivan et al. | |
| 7,652,581 B2 | 1/2010 | Gentry et al. | |
| 7,656,299 B2 | 2/2010 | Gentry et al. | |
| 7,714,238 B2 | 5/2010 | Skinner et al. | |
| 7,746,218 B2 | 6/2010 | Collins, Jr. et al. | |
| 7,752,926 B2 | 7/2010 | Caminade et al. | |
| 7,825,814 B2 | 11/2010 | Lokhorst et al. | |
| 7,849,545 B2 | 12/2010 | Flocard et al. | |
| 7,852,208 B2 | 12/2010 | Collins, Jr. et al. | |
| 7,868,740 B2 | 1/2011 | McNeely et al. | |
| 8,011,041 B2 | 9/2011 | Hann | |
| 8,117,701 B2 | 2/2012 | Bobey et al. | |
| 8,121,800 B2 | 2/2012 | Altman et al. | |
| 8,272,276 B2 | 9/2012 | Gorjanc et al. | |
| 8,413,271 B2 | 4/2013 | Blanchard et al. | |
| 2002/0034166 A1 | 3/2002 | Barany et al. | |
| 2002/0121146 A1 | 9/2002 | Manaresi et al. | |
| 2003/0105389 A1 | 6/2003 | Noonan et al. | |
| 2004/0046668 A1 | 3/2004 | Smith et al. | |
| 2004/0059199 A1 | 3/2004 | Thomas et al. | |
| 2005/0076715 A1 | 4/2005 | Kuklis et al. | |
| 2005/0165284 A1 | 7/2005 | Gefen | |
| 2006/0028350 A1 | 2/2006 | Bhai | |
| 2006/0065060 A1 | 3/2006 | Ito et al. | |
| 2006/0152378 A1 | 7/2006 | Lokhorst et al. | |
| 2006/0213286 A1 | 9/2006 | De Arenaza | |
| 2006/0293613 A1 | 12/2006 | Fatehi et al. | |
| 2007/0008156 A1 | 1/2007 | Ueda et al. | |
| 2007/0234825 A1 | 10/2007 | Loomis et al. | |
| 2007/0235231 A1 | 10/2007 | Loomis et al. | |
| 2008/0009686 A1 | 1/2008 | Hendrich | |
| 2008/0060138 A1 | 3/2008 | Price et al. | |
| 2008/0078030 A1 | 4/2008 | Lee et al. | |
| 2008/0169931 A1 | 7/2008 | Gentry et al. | |
| 2008/0183048 A1 | 7/2008 | Zhang | |
| 2008/0202251 A1 * | 8/2008 | Serban | G01L 1/142 73/780 |
| 2008/0275326 A1 | 11/2008 | Kasielke et al. | |
| 2009/0044334 A1 | 2/2009 | Parsell et al. | |
| 2009/0069727 A1 | 3/2009 | Neustaedter et al. | |
| 2009/0070939 A1 | 3/2009 | Hann | |
| 2009/0099480 A1 | 4/2009 | Salgo et al. | |
| 2009/0119843 A1 | 5/2009 | Rodgers et al. | |
| 2009/0129031 A1 | 5/2009 | Someya et al. | |
| 2009/0129556 A1 | 5/2009 | Ahn | |
| 2009/0256817 A1 * | 10/2009 | Perlin | G06F 3/0233 345/174 |
| 2010/0052917 A1 | 3/2010 | Sullivan et al. | |
| 2010/0162832 A1 | 7/2010 | Brauers | |
| 2010/0268122 A1 | 10/2010 | Drennan et al. | |
| 2010/0298742 A1 | 11/2010 | Perlman et al. | |
| 2011/0001622 A1 | 1/2011 | Gentry et al. | |
| 2011/0030141 A1 | 2/2011 | Soderberg et al. | |
| 2011/0035057 A1 | 2/2011 | Receveur et al. | |
| 2011/0046498 A1 | 2/2011 | Klap et al. | |
| 2011/0068932 A1 | 3/2011 | Flocard et al. | |
| 2011/0156915 A1 | 6/2011 | Brauers et al. | |
| 2011/0234408 A1 | 9/2011 | Dixon et al. | |
| 2011/0263950 A1 | 10/2011 | Larson et al. | |
| 2011/0302719 A1 | 12/2011 | Schwirian et al. | |
| 2011/0308019 A1 | 12/2011 | Terawaki et al. | |
| 2012/0184862 A1 | 7/2012 | Foo et al. | |
| 2012/0253142 A1 | 10/2012 | Meger et al. | |

(56) References Cited

U.S. PATENT DOCUMENTS

| | | |
|---|---|---|
| 2012/0277637 A1 | 11/2012 | Vahdatpour et al. |
| 2012/0323501 A1 | 12/2012 | Sarrafzadeh et al. |
| 2013/0091961 A1 | 4/2013 | Taylor |

FOREIGN PATENT DOCUMENTS

| | | |
|---|---|---|
| EP | 0264047 A2 | 4/1988 |
| EP | 0480471 A2 | 4/1992 |
| EP | 1211633 | 6/2004 |
| EP | 2392304 A1 | 12/2011 |
| JP | H02-078925 | 3/1990 |
| JP | 02232050 A | 9/1990 |
| JP | 6201502 A2 | 7/1994 |
| JP | H06281516 | 10/1994 |
| JP | H07-65943 | 7/1995 |
| JP | 10024073 A | 1/1998 |
| JP | 20020126007 A | 5/2002 |
| JP | 2004-245822 | 9/2004 |
| JP | 2004245822 A | 9/2004 |
| JP | 2004-363759 | 12/2004 |
| JP | 2005237684 A | 9/2005 |
| JP | 2006094903 | 4/2006 |
| JP | 2008027030 A | 2/2008 |
| JP | 2008-216016 | 9/2008 |
| JP | 2010012335 A | 1/2010 |
| JP | 2010-043881 | 2/2010 |
| WO | 2007106040 A1 | 9/2007 |
| WO | 2007121586 | 11/2007 |
| WO | 2009048617 | 4/2009 |
| WO | 2009065109 | 5/2009 |
| WO | 2009138976 A2 | 11/2009 |
| WO | 2010092517 A1 | 8/2010 |
| WO | 2010102309 A1 | 9/2010 |
| WO | 2010119441 A2 | 10/2010 |
| WO | 2010119441 A3 | 10/2010 |
| WO | 2011091517 | 8/2011 |
| WO | 2011111021 | 9/2011 |
| WO | 2011113070 | 9/2011 |
| WO | 2012056405 | 5/2012 |
| WO | 2012114298 | 8/2012 |
| WO | 2013008187 | 1/2013 |
| WO | 2013021376 A1 | 2/2013 |
| WO | 2013105028 | 7/2013 |
| WO | 2013156907 | 10/2013 |
| WO | 2014024094 | 2/2014 |
| WO | 2014024094 A2 | 2/2014 |
| WO | 2014064596 A2 | 5/2014 |

OTHER PUBLICATIONS

Office Action for U.S. Appl. No. 13/881,169 dated May 7, 2015.
International Search Report for PCT/IB2015/051822 dated Jul. 6, 2015, 4 pages.
International Written Opinion for PCT/IB2015/051822 dated Jul. 6, 2015, 6 pages.
European Patent Office, Office Action for the corresponding European Patent Application No. 10 720 826.6 dated Apr. 16, 2014.
International Searching Authority, The International Search Report and the Written Opinion for the corresponding International Application No. PCT/IB13/59499 mailed May 20, 2014.
Muhammad Ahsen Khan, Dyeing of Wood and Silk Fibres with a Conductive Polyelectrolyte and Comparing Their Conductance, Report No. 2011.7.10, Masters in Textile Technology, University of Boras 2011.
Mehdi Nouri, et al. Iranian Polymer Journal, Archive of SID, Conductivity of Textile Fibers Treated with Aniline, vol. 9, No. 1, Feb. 8, 2000.
Final Office Action for U.S. Appl. No. 13/881,169 dated Sep. 24, 2015.
International Search Report and Written Opinion for PCT/IL2010/000294 dated Oct. 26, 2010.
International Search Report and Written Opinion for PCT/IB2011/051016 dated Oct. 9, 2012.
International Search Report and Written Opinion for PCT/IB2011/054773 dated Jun. 15, 2012.
International Search Report and Written Opinion for PCT/IB12/50829 dated Sep. 17, 2012.
International Search Report and Written Opinion for PCT/IB2012/053538 dated Dec. 17, 2012.
International Search Report and Written Opinion for PCT/IB2013/050173 dated Jul. 1, 2013.
International Search Report and Written Opinion for PCT/IB2013/52878 dated Oct. 29, 2013.
International Search Report and Written Opinion for PCT/IB2013/056287 dated Feb. 10, 2014.

* cited by examiner

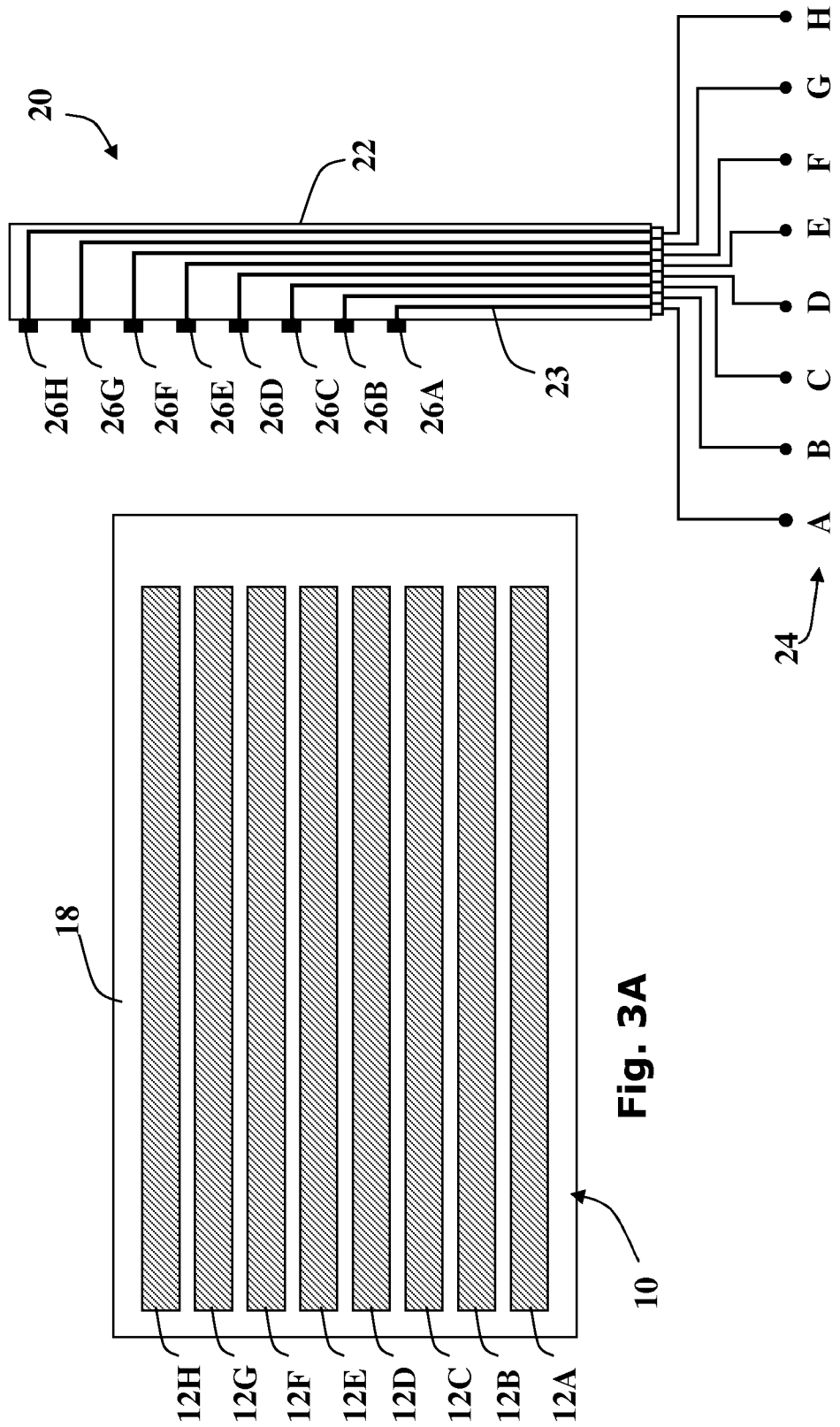

METHODS AND SYSTEMS FOR THE MANUFACTURE AND INITIATION OF A PRESSURE DETECTION MAT

CROSS-REFERENCE TO RELATED APPLICATIONS

This application is the U.S. national phase of PCT Appln. No. PCT/IB2012/053538 filed Jul. 11, 2012 which claims the benefit of U.S. Provisional Application No. 61/507,418 filed Jul. 13, 2011, the disclosures of which are incorporated in their entirety by reference herein.

FIELD OF THE INVENTION

The embodiments disclosed herein relate to pressure sensing mats, in particular the disclosure relates to the manufacture and system testing of a pressure sensing mat comprising crossed parallel strip electrodes forming a pressure sensing matrix.

BACKGROUND

A pressure sensing mat comprising crossed parallel strip electrodes forming a pressure sensing matrix is described for example in the applicant's copending PCT patent application number PCT/IL2010/000294 although the current disclosure may be applicable to other sensing mats.

Where pressure sensing mats are used it is important to ensure equipment meets quality standards. It will be appreciated that there is therefore a need for a method of manufacture which integrates construction with continued quality assurance and system testing. The disclosure herein addresses this need.

SUMMARY OF THE INVENTION

According to a first aspect of the current disclosure, a method is presented for the manufacture of a pressure sensing mat, the method comprising the steps of: (a) preparing two conductive layers, each conductive layer comprising an array of conducting strips mounted upon a substrate arranged in a parallel fashion, wherein the conducting strips of the first conductive layer are oriented perpendicularly in relation to the conducting strips of the second conductive layer; (b) for each conductive layer, connecting each of said conducting strips to a communication line; (c) sandwiching a compressible layer between said two conductive layers; and (d) performing a pressure reading standardization test to said mat.

In certain embodiments, the conductive strips are laminated with an insulating material.

In certain embodiments, the step of preparing two conductive layers, step (a) above, comprises the steps of: (i) affixing said conductive strips to a substrate in a parallel orientation; and (ii) measuring the resistance between at least one pair of adjacent conductive strips.

In certain embodiments, the conductive strips are connected to a test monitor through a test probe. Alternatively, two of said conductive strips are connected to a test monitor through a test probe, and the test probe is moved sequentially from one pair of adjacent conductive strips to the next until all the strips have been tested.

In certain embodiments, the step of, for each conductive layer, connecting each of said conducting strips to a communication line, step (b) above, is followed by a testing procedure comprising the steps of: (i) placing a conducting plate across said conducting strips; (ii) applying an alternating potential to said conducting plate; and (iii) measuring voltage between each of the conducting strips and ground.

In certain embodiments, the step of, for each conductive layer, connecting each of said conducting strips to a communication line, step (b) above, is followed by a testing procedure comprising the steps of: (i) placing a conducting plate across said conducting strips; (ii) applying an alternating potential to each of said conducting strips; and (iii) for each conducting strip measuring voltage between the conducting plate and ground.

In certain embodiments, the step of, for each conductive layer, connecting each of said conducting strips to a communication line, step (b) above, is followed by a testing procedure comprising the steps of: (i) placing a conducting plate across said conducting strips; (ii) applying an alternating potential to all conducting strips except one selected conducting strip; and (iii) measuring voltage between the selected strip and ground.

In certain embodiments, the step of, for each conductive layer, connecting each of said conducting strips to a communication line, step (b) above, is followed by a testing procedure comprising the steps of: (i) placing a conducting plate across said conducting strips; (ii) applying an alternating potential to one selected conducting strip; and (iii) measuring voltage between all conducting strips except the selected strip and ground.

In certain embodiments, the conducting plate is laminated with an insulating material.

In certain embodiments, the step of performing a pressure reading standardization test to said mat, step (d) above, comprises the steps of: (i) exerting a known pressure upon at least one region of said pressure detection mat; (ii) measuring a pressure reading recorded by said pressure detection mat; and (iii) comparing said pressure reading with a look up table.

According to a second aspect of the current disclosure, a method is disclosed for testing a pressure sensing mat comprising a first conductive layer comprising an array of parallel conducting strips, a compressible layer situated upon the first array and a second conductive layer comprising an array of parallel conducting strips situated upon the compressible layer, the conducting strips of each conductive layer being connected to a communication line, the method comprising the step of: (a) for each conductive layer, measuring the resistance between at least one pair of adjacent conducting strips.

In certain embodiments, the conductive strips are laminated with an insulating material.

In certain embodiments, for the step of, for each conductive layer, measuring the resistance between at least one pair of adjacent conducting strips, step (a) above, each of said conductive strips is connected to a test monitor through a test probe. Alternatively, two of said conductive strips are connected to a test monitor through a test probe, and the test probe is moved sequentially from one pair of adjacent conductive strips to the next until all the strips have been tested.

In certain embodiments, the method of testing the pressure sensing mat further comprises the step of: (b) testing the electrical connection between each of said conducting strips and the communication line.

Optionally, step (b) comprises the steps of: (i) placing a conducting plate across said conducting strips; (ii) applying an alternating potential to said conducting plate; and (iii) measuring voltage between each of the conducting strips and ground.

Optionally, step (b) comprises the steps of: (i) placing a conducting plate across said conducting strips; (ii) applying an alternating potential to each of said conducting strips; and (iii) for each conducting strip measuring voltage between the conducting plate and ground.

Optionally, step (b) comprises the steps of: (i) placing a conducting plate across said conducting strips; (ii) applying an alternating potential to all conducting strips except one selected conducting strip; and (iii) measuring voltage between the selected strip and ground.

Optionally, step (b) comprises the steps of: (i) placing a conducting plate across said conducting strips; (ii) applying an alternating potential to one selected conducting strip; and (iii) measuring voltage between all conducting strips except the selected strip and ground.

In certain embodiments, the method of testing the pressure sensing mat further comprises the step of: (c) performing a pressure reading standardization test to said mat.

Optionally, step (c) comprises the steps of: (i) exerting a known pressure upon at least one region of said pressure detection mat; (ii) measuring a pressure reading recorded by said pressure detection mat; and (iii) comparing said pressure reading with a look up table.

BRIEF DESCRIPTION OF THE FIGURES

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the several selected embodiments may be put into practice. In the accompanying drawings.

DETAILED DESCRIPTION

Figure 1:
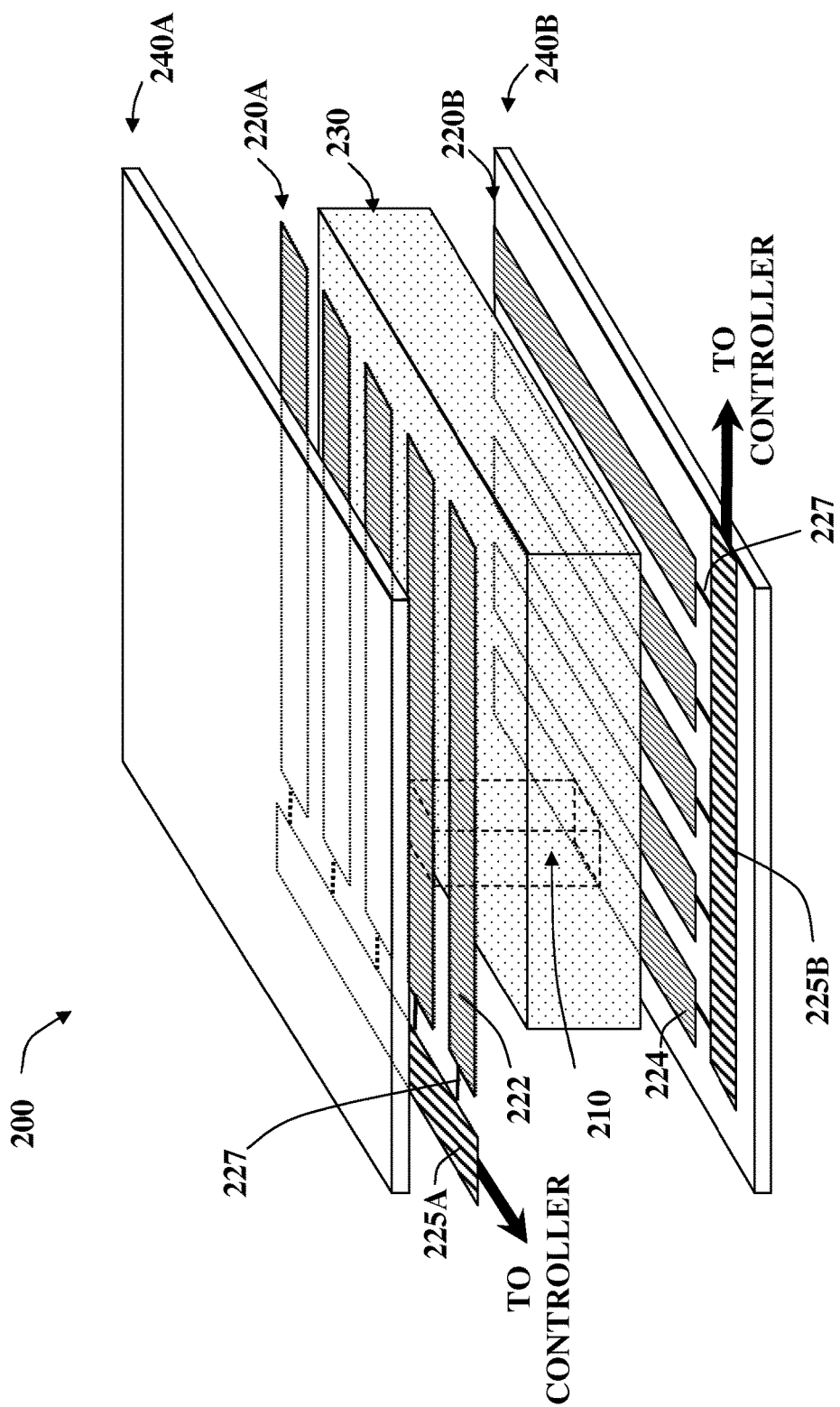
FIG. 1 is an exploded isometric projection schematically representing an embodiment of a pressure-detection mat.

Reference is now made to FIG. 1 which shows an exploded isometric projection schematically representing an embodiment of a pressure-detection mat 200 comprising a plurality of sensors 210 arranged in a form of a matrix. The mat 200 of the embodiment includes two arrays 220A, 220B of conductive strips 222, 224 affixed on a substrate 240A, 240B, two controller communication lines 225A, 225B and a compressible layer 230. Each conductive strip 222, 224 may be laminated with an insulating material. The compressible layer 230 may comprise an insulating, compressible material.

The two conductive layers 220A, 220B made of conductive material are separated by the compressible layer 230. Each of the conductive layers 220A, 220B typically consists of an array of parallel conductive strips 222, 224 (respectively). Further, the two arrays may be arranged orthogonally such that in the first conductive layer 220A, the array of conductive strips 222 are horizontal and in the second conductive layer 220B, the array of conductive strips 224 are vertical. It is particularly noted that each conducting strip 222, 224 is insulated from, and not in conductive contact with, other conducting strips in its respective layer.

The controller communication lines 225A, 225B provide a line of communication between the sensors 210 and a system controller (not shown). Each of the conductive strips 222, 224 may be connected to a controller communication line 225A, 225B via an individual connector 227. Optionally, the communication lines 225A, 225B may comprise a bundle of conductors such as a multi-core cable, a flat cable or the like.

Each sensor 210 may be a capacitance sensor based upon the capacitance between the overlapping sections of the conducting strips at each junction of a vertical conductive strip 222 with a horizontal conductive strip 224. These capacitance sensors are configured such that pressing anywhere on their surface changes the spacing between the two conductive layers 220A, 220B, and consequently the capacitance of the intersection. A controller may provide an electric potential selectively to each vertical strip via a first communication line 225A and the electrical potential may be monitored on each horizontal strip via a second communication line 225B such that the capacitance of the sensor 210 of the overlapping section may be determined.

It is noted that by providing an oscillating electric potential across each sensor and monitoring the alternating current produced thereby, the impedance of the intersection may be calculated and the capacitance of the intersection determined. The alternating current varies with the potential across a capacitor according to the formula:

$$I_{ac} = 2\pi f C V_{ac}$$

where $I_{ac}$ is the root mean squared value of the alternating current, $V_{ac}$ is the root mean squared value of the oscillating potential across the capacitor, f is the frequency of the oscillating potential and C is the capacitance of the capacitor.

Thus where the values of $V_{ac}$ and $I_{ac}$ are known at a known frequency f, the capacitance C of a sensor may be calculated. Accordingly, where the mechanical properties of the sensor are known, the pressure applied upon the sensor may be deduced.

It will be appreciated that during the manufacture and initialization of a pressure detection mat such as described hereinabove, there is a need to ensure that each conducting strip is electrically isolated from the other conducting strips and electrically connected to the communication lines. Furthermore, the relationship between capacitance values determined for the sensors and the pressure exerted upon the mat should be determined.

The disclosure hereinbelow presents possible systems and methods for the manufacture and system testing of a pressure sensing mat.

Figure 2:
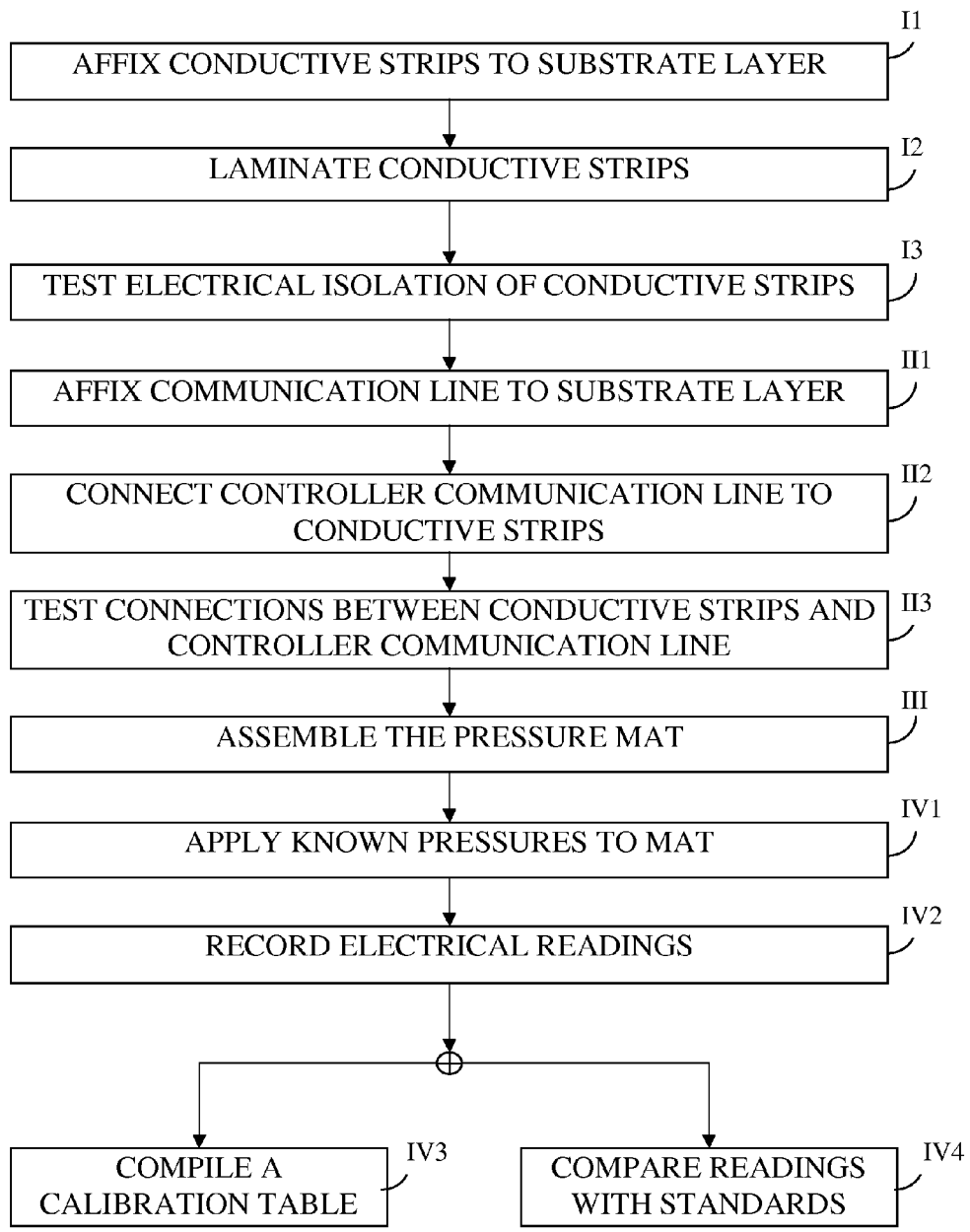
FIG. 2 is a flowchart of a method of manufacture and system testing of a pressure sensing mat.

Referring now to the flowchart of FIG. 2, a method of manufacture and system testing of a pressure sensing mat is presented. The method includes four phases:

I. Conductive Strip Preparation
II. Communication Line Preparation
III. Pressure Mat Assembly
IV. Pressure Reading Standardization During the Conductive Strip Preparation phase, the conductive strips 222, 224 may be affixed to a substrate I1 and tested for stray connections which may form short circuits between adjacent strips I3. The substrate may be formed from a variety of suitable materials, such as a sheet of fabric, polymer, plastic, leather, thermo poly urethane (TPU) or the like. Optionally, the conductive strips may be laminated I2 to improve electrical insulation and to protect the conductors. One possible system for testing the electrical isolation of the conductive strips is described hereinbelow in relation to FIGS. 3A-D.

During the Communication Line Preparation phase, a communication line 225A, 225B may be affixed to the substrate II1, connected to the conductive strips 222, 224, II2 and the connections tested II3. Possible systems for testing the connections between the communication line and the conducting strips are described hereinbelow in relation to FIGS. 5A and 5B During the Pressure Mat Assembly phase III, a compressible layer, such as a sheet of foam, or some such spongy material is sandwiched between two prepared layers having crossed conductive strips. Where required, the layers may be sewn together; alternatively, the layers may be left unsewn until after the Pressure Reading Standardization phase.

During the Pressure Reading Standardization phase, known pressures may be applied to the assembled pressure mat IV1 and electrical readings recorded IV2. In this way, the electrical readings of the mat may be calibrated to pressure measurements IV3. Alternatively or additionally, thereby the mat may be tested to conform to predefined standards IV4. Possible standardization tests are described hereinbelow.

Reference is now made to FIG. 3A which schematically represents an embodiment of one conductive layer 10 of a pressure sensing mat during the Conductive Strip Preparation phase of manufacture. An array of conductive strips 12A-H may be affixed to a substrate 18 with each conductive strip 12A-H electrically isolated from its neighbors. Accordingly, the substrate 18 may be constructed from an insulating material such as fabric, polymer, plastic, leather, thermo poly urethane (TPU) or the like.

Referring now to FIG. 3B, a first embodiment of a test probe 20 for use in testing the conductive layer 10 is schematically represented. Stray connections between the conductive strips 12A-H may be identified using such a test probe 20. The test probe 20 may include a plurality of terminals 24, a row of probe conductors 26A-H and a bundle of test lines 23. The terminals 24 are connected to the probe conductors 26A-H via dedicated test lines 23 which are optionally contained by, affixed to or otherwise secured to some platform 22.

Figure 3C:
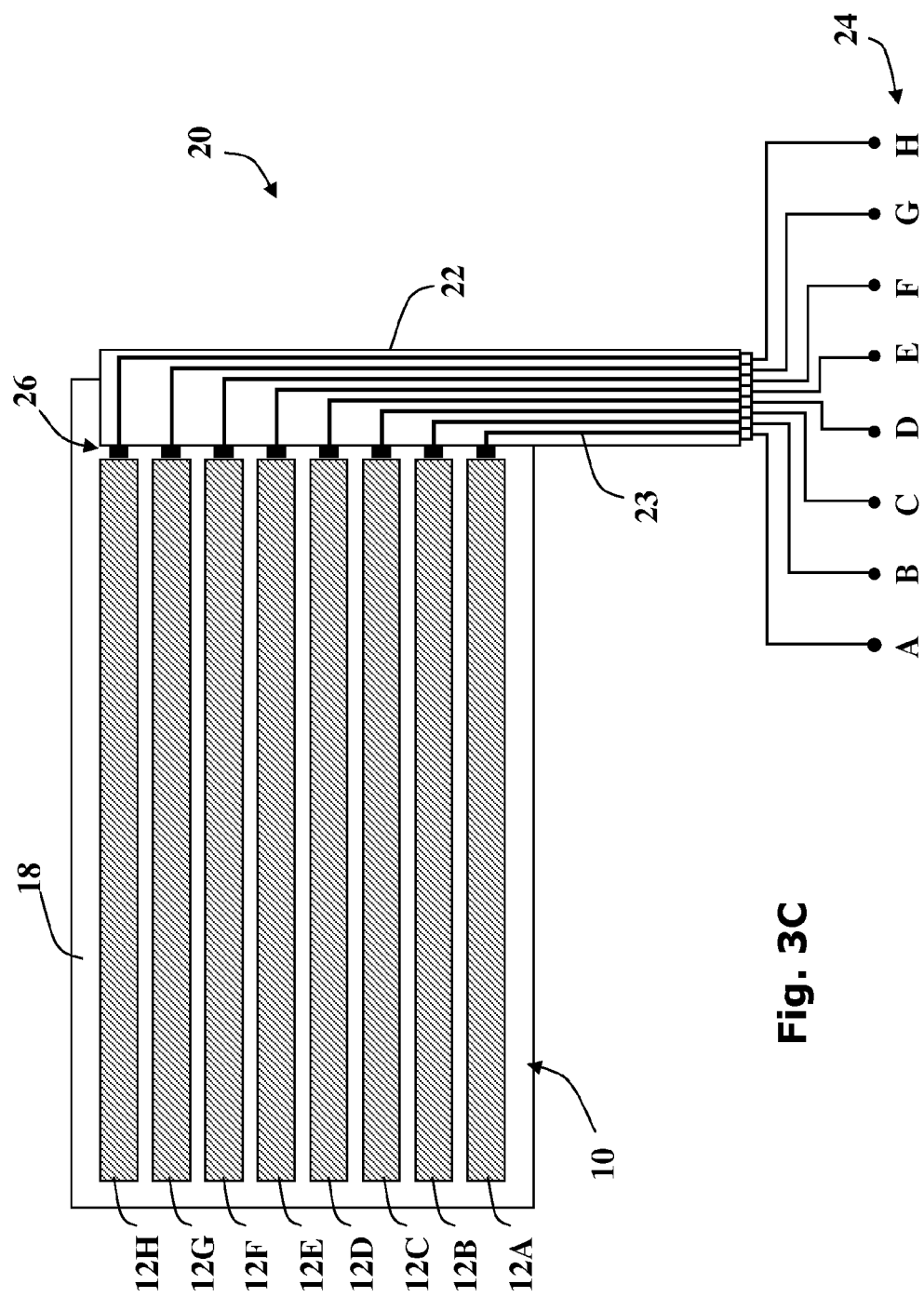
FIGS. 3C and D show the test probe being used to test the pressure sensing mat.

With reference to FIG. 3C, a schematic representation is shown of the test probe 20 being used to check the isolation of the conductive strips 12A-H of the conductive layer 10. The test probe 20 is juxtaposed to the conductive layer 10 such that the probe conductors 26A-H are brought into contact with the conductive strips 12A-H.

A test monitor (not shown), which may comprise a processor, computer, microprocessor or other controller, may be connected to the probe 20 and operable to select and test pairs of adjacent probe terminals 24. It will be appreciated that each pair of adjacent probe terminals 24 corresponds to a pair of adjacent conducting strips 12. For example, in the embodiment represented in FIG. 3C, terminals A and B correspond to conducting strips 12A and 12B, terminals B and C correspond to conducting strips 12B and 12C, terminals C and D correspond to conducting strips 12C and 12D, terminals D and E correspond to conducting strips 12D and 12E, terminals E and F correspond to conducting strips 12E and 12F, terminals F and G correspond to conducting strips 12F and 12G and terminals G and H correspond to conducting strips 12G and 12H.

Accordingly, by applying a potential difference between each selected pair of terminals and measuring the current produced thereby, the resistance between the corresponding conducting strips may be monitored. Any stray connections forming short circuits between the conducting strips may be readily detected as particularly low resistance connections.

Figure 3D:
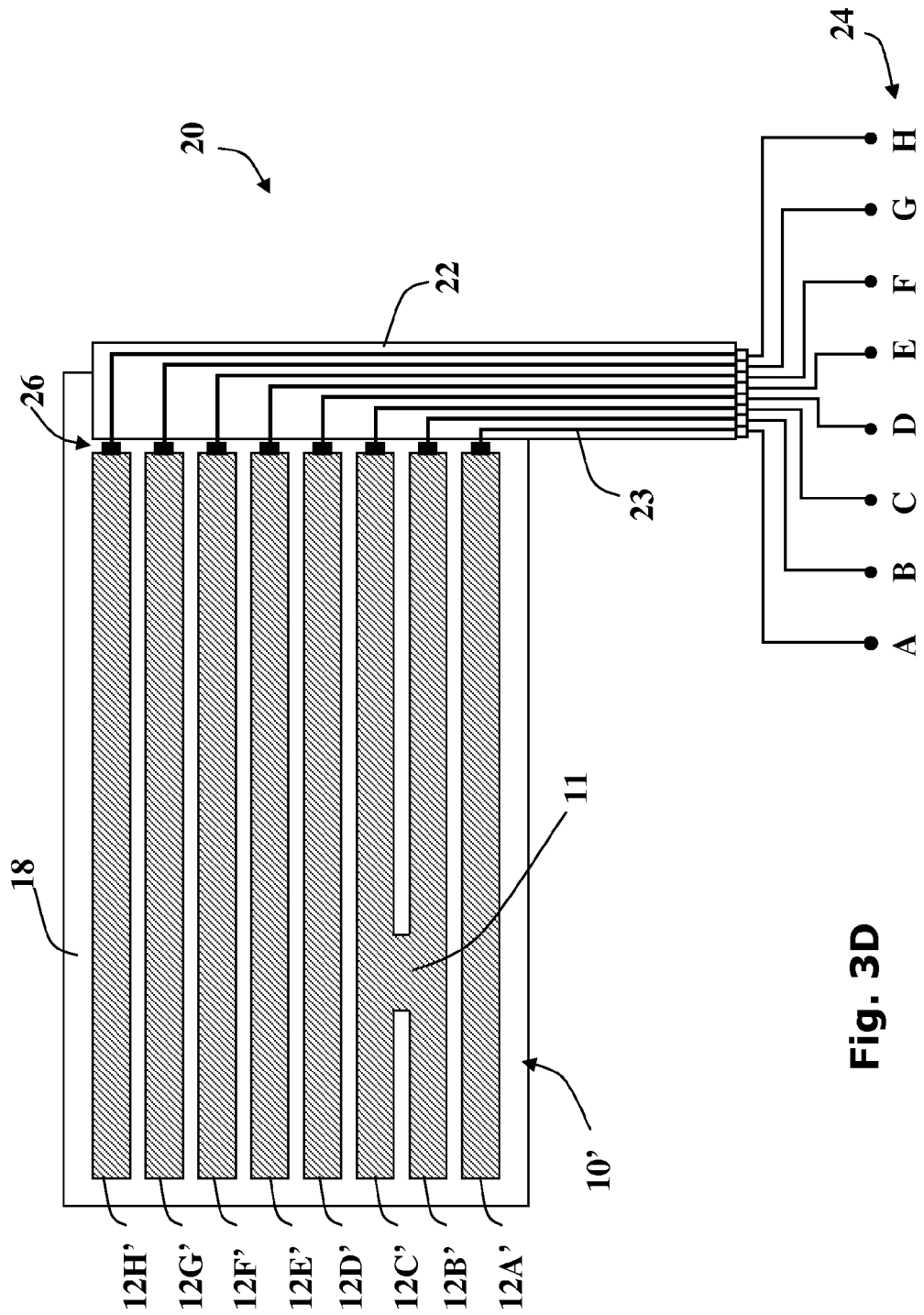
FIG. 3A is a schematic representation of one possible layer of a pressure sensing mat during preparation.
FIG. 3B is a schematic representation of a possible test probe for use testing the electrical isolation of conductive strips of the pressure sensing mat.
FIG. 3E is a schematic representation of another possible test probe.

Referring now to FIG. 3D, a faulty conductive layer 10' incorporating conducting strips 12A'-H' is represented. Most of the conducting strips of the conductive layer 10' are electrically isolated, however, there is a conducting bridge 11 between two of the conducting strips 12B' and 12C'. Because of this short circuit, the resistance between probe terminals B and C would be significantly lower than that between the other terminals. This would be reflected in a high current for a given potential difference applied thereacross.

Using such a test probe, the faulty conductive layer 10' may be identified and the fault pinpointed so that it may be fixed before connection of the communication line or assembly of the pressure sensing mat.

Figure 3E:
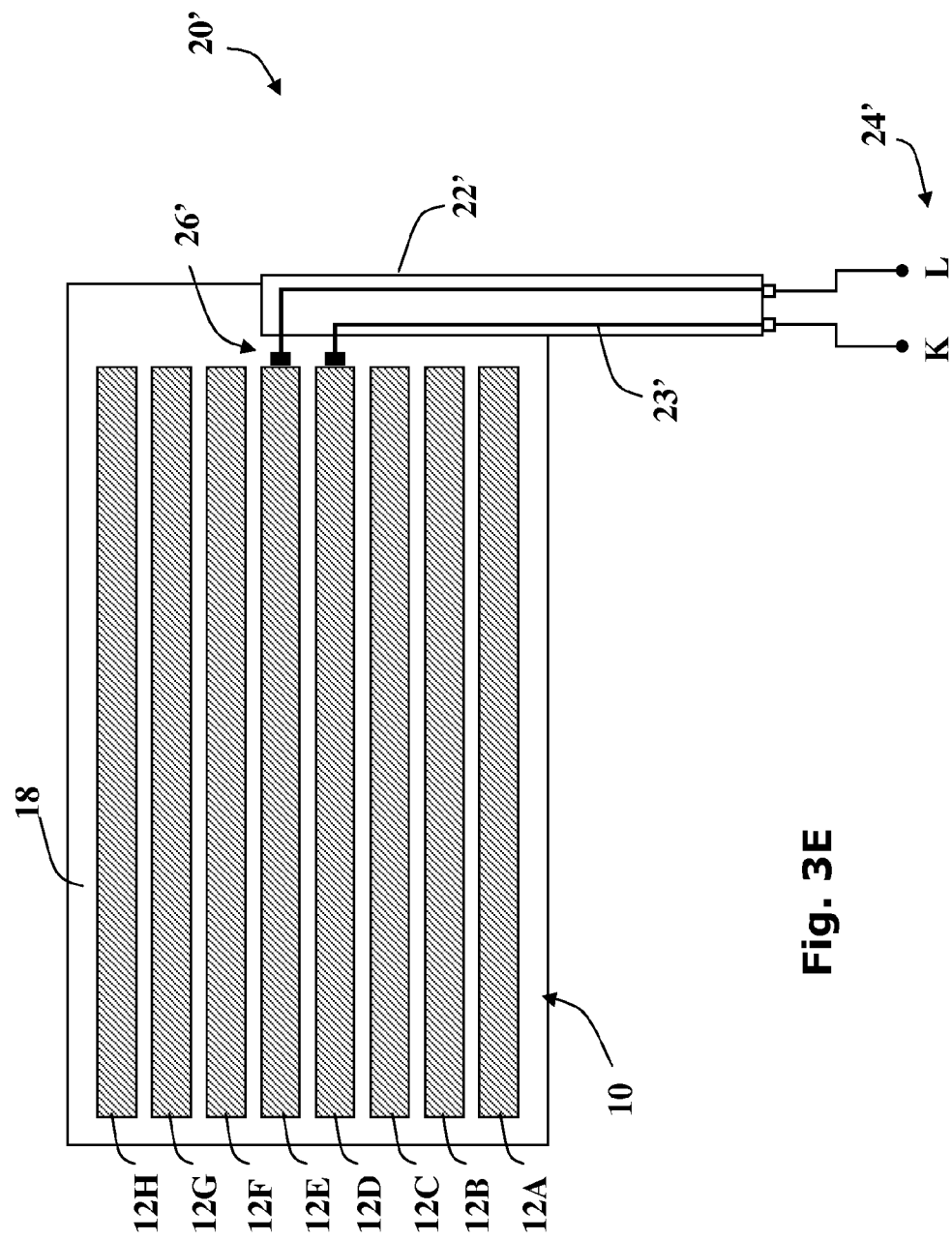

It will be appreciated that although only a multi-terminal test probe is described hereinabove, various other test probes may be used as suit requirements. Referring now to FIG. 3E, a schematic representation of an alternative test probe 20' is presented in which two probe conductors 26' are connected to two corresponding probe terminals 24' via two test lines 23'. The alternative test probe 20' may be used to test one pair of conducting strips 12 at a time. Current produced when a known potential difference is applied across the terminals K, L may be used to test the resistance between strips and thereby to detect short circuits. The probe 20' may be moved from pair to pair sequentially until all the strips have been tested. Optionally the probe may be mechanized, perhaps using rollers, tracks, articulated arms or the like, to move between the pairs of conducting strips during the test phase. Still other embodiments of the test probe will occur to those skilled in the art.

Figure 4:
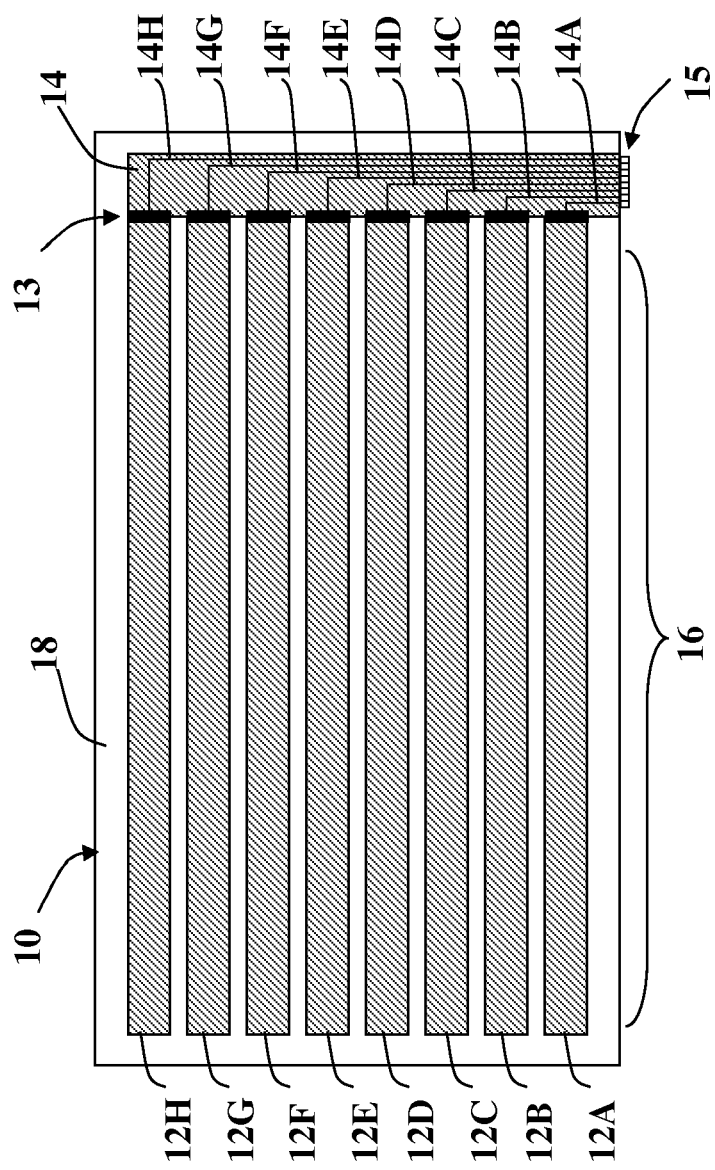
FIG. 4 is a schematic representation of an embodiment of the layer including the conducting strips and a controller communication line.

Reference is now made to FIG. 4 showing an embodiment of the conductive layer 10 including the conducting strips 12A-H and a controller communication line 14. The controller communication line 14, such a multi-wire flat cable or the like, may be affixed to the conductive layer 10, for example of TPU, following the lamination of the conducting strips 12A-H and the testing of their electrical isolation. The controller communication line 14 includes a bundle of individual conducting wires 14A-H for connecting the conducting strips 12A-H to a system controller (not shown) via a set of junctions 15 such as a flat band connector or the like. Each conductor of the controller communication line 14 is connected to an associated conducting strip 12 of the conductive layer 10.

In order to provide reliable communication between the controller and the pressure sensor there is a need for good electrical connection 13 between each conducting strip 12A-H and the controller communication line 14. Testing the quality of the connection 13 is a surprisingly difficult task, in part this is because the distal portion 16 of the conducting strips 12A-H may be laminated or otherwise insulated. Consequently, it may not be possible to connect a probe to the distal portion 16 of the conducting strips 12A-H.

In order to overcome this problem, various creative solutions are taught herein allowing the conductive connections between the strips and the communication lines to be tested. It will be appreciated that such solutions may have application beyond the scope of the pressure sensing systems such as described herein.

Figure 5A:
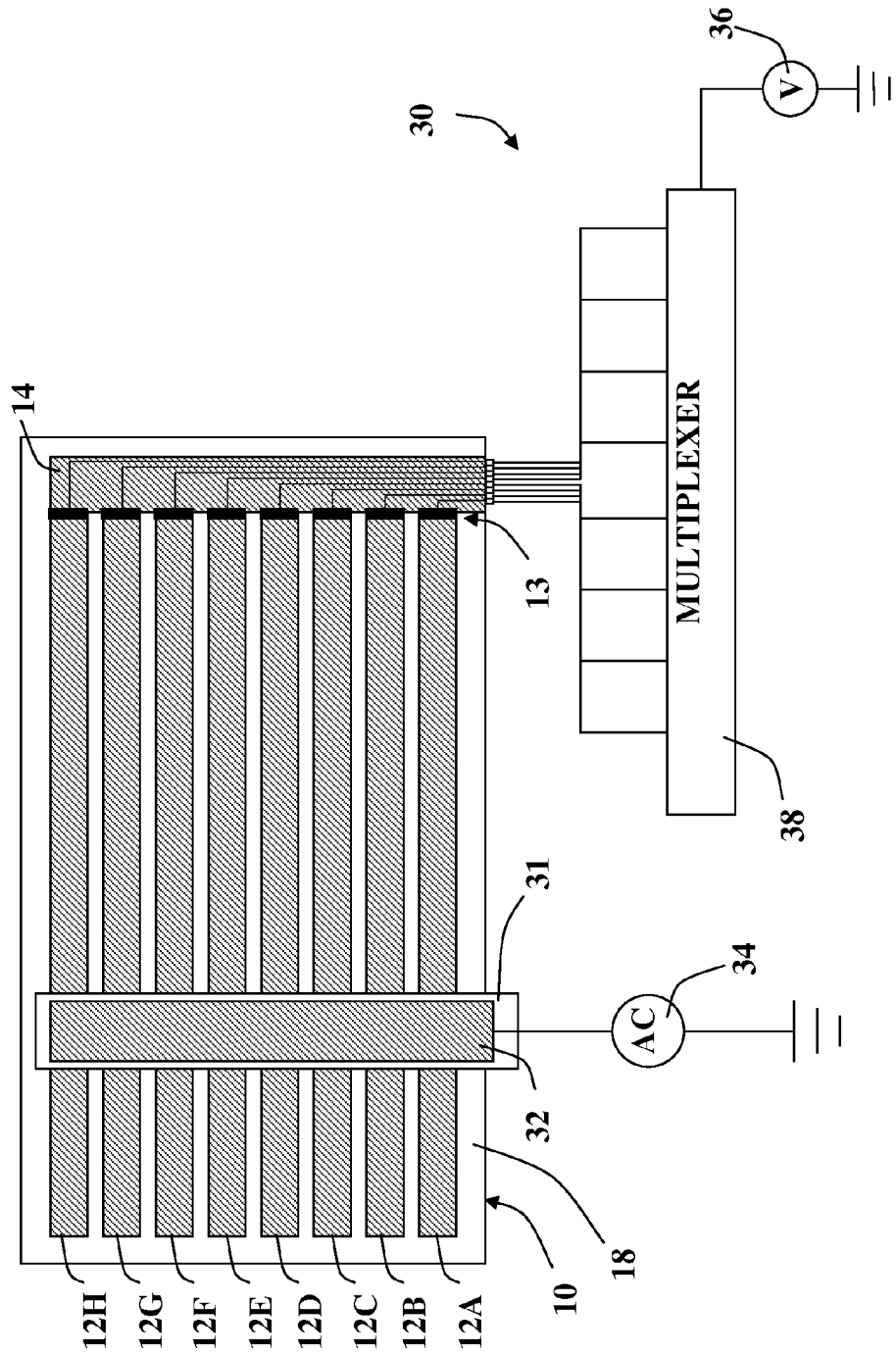
FIGS. 5A-C show various methods for testing the connections between the conducting strips and the controller communication line.

Reference is now made to FIG. 5A showing a possible monitoring system 30 for use in testing the connections 13 between the conducting strips 12 of the conductive layer 10 and the communication line 14. The system 30 includes a conducting plate 32, an insulating layer 31, an alternating current (AC) source 34, a switching unit 38 and a voltage monitor 36.

The conducting plate 32 is laid across the conducting strips 12 and electrically isolated therefrom by an insulating layer 31. Variously, the insulating layer 31 may be a separate sheet of insulating material, a laminate coating of the conducting plate 32, the conducting strips 12 or combinations thereof, as suit requirements.

The conducting plate 32 may be wired to an AC source 34. The switching unit 38, such as a multiplexer for example, is connected to control communication line 14, possibly via a flat cable connection or the like. The switching unit 38 may selectively connect each conducting strip via the controller communication line 14 to the voltage monitor 36.

The conducting plate 32 forms a capacitor with each of the conducting strips 12A-H. Thus although the conducting plate 32 is insulated from the conducting strips 12A-H the alternating voltage applied thereto produces a significant response in the voltage monitor 36. The voltage recorded by the system 30 may serve as an indication of quality of the connections 13 between the conducting strips 12A-H and the control communication line 14. If all the connections are good, the voltage monitor 36 may record similar values regardless of which conducting strip is connected thereto. Where a connection is not good, the voltage monitor may produce an anomalous record, for example not recording a voltage, recording a low voltage, recording a high voltage or the like.

Figure 5B:
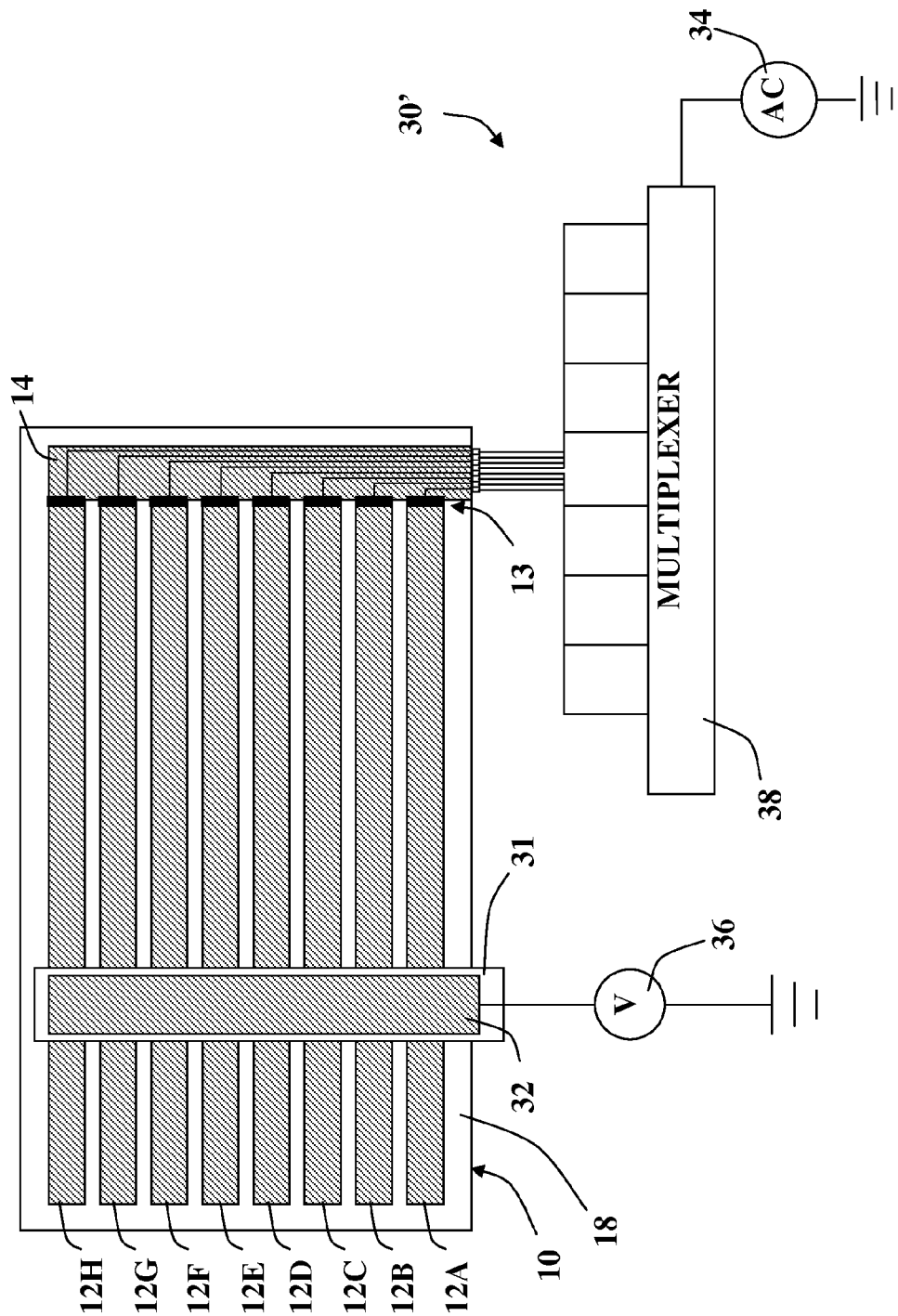

With reference to FIG. 5B, an alternative embodiment of the monitoring system 30' may exchange the AC 34 source and the voltage monitor 36 such that the AC voltage is selectively applied to each conducting strip 12A-H and the voltage recorded in the conducting plate 32.

Figure 5C:
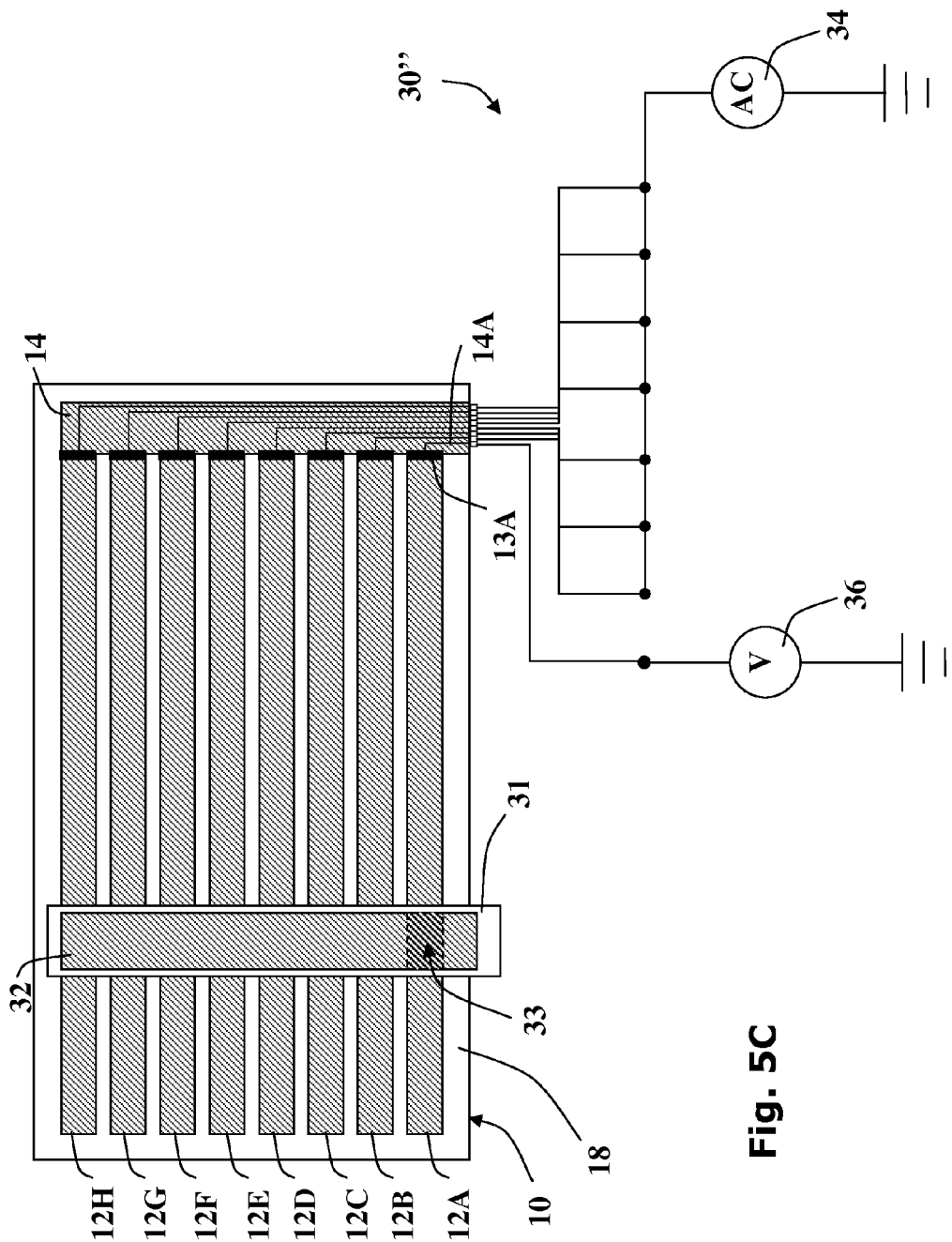

Referring now to FIG. 5C, still another embodiment of the monitoring system 30" is shown. One conducting strip 12A is connected to the voltage monitor 36 and all of the other conducing strips 12B-H are connected to the AC source 34. A switching system (not shown) may be operable to selectively connect each conducting strip 12A-H in turn to the voltage monitor 36 with the others connected to the AC source 34. Anomalous voltage readings may indicate a faulty connection between the selected conducting strip 12 and the control communication line 14.

Optionally, a conducting plate 32 may be placed across all the conducting strips 12A-H which may improve voltage readings. By placing the conducting plate 32 laterally across the conducting strips, the capacitance of the overlapping area between the strip 12A being tested and the plate 32 is relatively large in comparison with the capacitance between the associated connecting wire 14A and the rest of the bundle 14. Thus if the connection 13A between one connecting wire 14A and its associated conducting strip 12A is broken, then the voltage reading will be significantly different from that of unbroken connections.

Alternatively, the capacitance between the conductive strip 12A being tested and the other conductive strips 12B-H may be sufficient to produce significant voltage readings.

It will be appreciated that the solution described in relation to FIG. 5C may be readily applied to testing connections in multicore cables, such as telephone lines and the like, from one end. This may be particularly useful when testing the connections with long cables where it may not be practical to connect probes both ends. Connections may be tested by connecting all cores but one to an AC voltage source and measuring the voltage produced in the remaining core. Anomalous voltage readings may be indicative of faulty connections.

As noted hereinabove a pressure sensing mat may be assembled by sandwiching a compressible layer, such as a sheet of foam, or some such spongy material, between two prepared conductive layers having crossed conductive strips as described hereinabove in relation to in FIG. 1.

Figure 6:
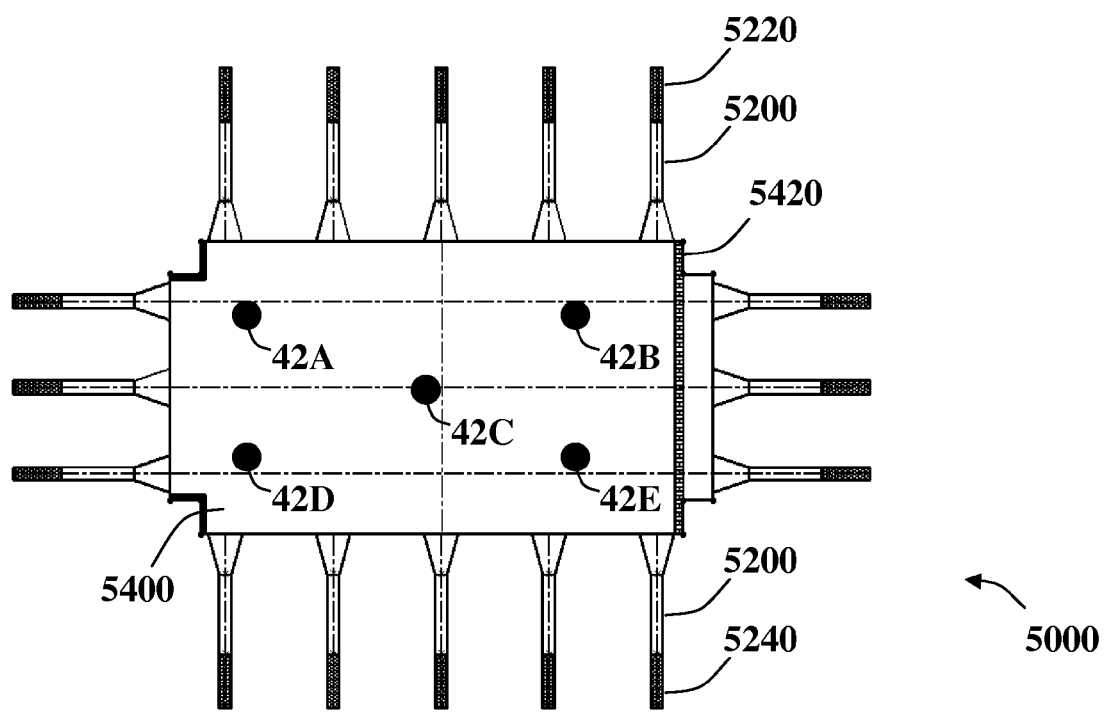
FIG. 6 is a top view of an embodiment of a pressure sensing module incorporated into a mattress overlay.

Reference is now made to FIG. 6, showing a top view of an embodiment of a pressure sensing module incorporated into a mattress overlay 5000. A sensor matrix (not shown) is housed within a cover sheet 5400 and which may be sealed by a zipper 5420 or alternatively sewn into the cover as required. The sensor module may be connected to a hardware controller (not shown) via the controller communication line (not shown).

The pressure detection mat 5000 may be attached to a surface in such a way that prevents movement of the mat relative to the surface. A feature of the embodiment of the mat 5000 is that the cover sheet 5400 may include a coupling mechanism for securing the mat to a seat or a back of a mattress, a bed, a chair, a bench, a sofa, a wheelchair or the like. The coupling mechanism may include for example at least one strap 5200 having an attachment means 5240 configured to secure the straps 5200 to the seat or to each other such that the pressure detection mat is held securely. This may be useful to prevent folding, wrinkling or other movement of the detection mat which may contribute to the creation of shear forces which are known to encourage the formation of external pressure sores. Suitable attachment means include for example, hook-and-eye materials such as Velcro®, buckles, adhesives, buttons, laces or the like, as suit requirements.

A variety of standardization tests may be performed upon the pressure detection mat 5000 for the purposes of calibration, quality assurance and the like. According to one such test, weights 42A-E of known value and size are applied to a plurality of test points upon the mat and the responses recorded. Optionally, between three to ten test points may be tested for standard testing. In one example, six test points are selected and weights no smaller than the size of one pixel of the sensor matrix are applied thereupon.

According to requirements, the standardization tests may be carried out before the pressure sensing matrix is sewn into the overlay. Alternatively or additionally standardization tests may be carried out after the sensing matrix is sewn into the overlay.

Pressure may be applied, for example, and progressively more weights may be placed upon the mat until, say, five sample pressure values have been tested for each test point. Alternatively, in other embodiments, a mechanical mechanism such as a spring, hydraulic cylinder, pneumatic cylinder or the like, may apply a known force upon a pressing member urged onto the pressure detection mat. Still other pressure application methods will occur to those skilled in the art.

The readings, thus produced, may be used variously for calibration of the particular mat or to check the mats conformity to standards. For example a look up table may be compiled to calibrate the particular mat. Accordingly, calibration data may be stored for reference by a controller associated with that mat. Alternatively, the readings may be compared to a precompiled look-up table to check if they lie within a certain tolerance of the data values in that table.

The scope of the disclosed subject matter is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A method for manufacture of a pressure sensing mat, the method comprising the steps of:
    (a) preparing two conductive layers, each conductive layer comprising an array of conducting strips mounted upon a substrate arranged in a parallel orientation, wherein the conducting strips of the first conductive layer are oriented perpendicularly in relation to the conducting strips of the second conductive layer;
    (b) connecting at least two of the conducting strips within one of the two conductive layers by:
        (i) placing a conducting plate across the conducting strip;
        (ii) applying an alternating potential to the conducting plate; and
        (iii) measuring voltage between each of the conducting strips and ground;
    (c) sandwiching a compressible layer between said two conductive layers; and
    (d) performing a pressure reading standardization test on the mat.

2. The method of claim 1, further comprising (e) laminating each of the conductive strips with an insulating material.

3. The method of claim 1, further comprising
    (e) measuring the resistance between at least one pair of adjacent conductive strips.

4. The method of claim 3, wherein each of the conductive strips is connected to a test monitor through a test probe.

5. The method of claim 4, further comprising (f) moving the test probe sequentially from one pair of adjacent conductive strips to the next until all the strips have been tested.

6. The method of claim 1 wherein step (d) comprises the steps of:
    (i) exerting a known pressure upon at least one region of the pressure detection mat;
    (ii) measuring pressure reading recorded by the pressure detection mat; and
    (iii) comparing the pressure reading with a look up table.

7. A method for manufacture of a pressure sensing mat, the method comprising the steps of:
    (a) preparing two conductive layers, each conductive layer comprising an array of conducting strips mounted upon a substrate arranged in a parallel orientation, wherein the conducting strips of the first conductive layer are oriented perpendicularly in relation to the conducting strips of the second conductive layer;
    (b) connecting at least two of the conducting strips to a communication line by:
        (i) placing a conducting plate across the conducting strips;
        (ii) applying an alternating potential to each of the conducting strips; and
        (iii) for each conducting strip measuring voltage between the conducting plate and ground;
    (c) sandwiching a compressible layer between the two conductive layers; and
    (d) performing a pressure reading standardization test on the mat.

8. A method for manufacture of a pressure sensing mat, the method comprising the steps of:
    (a) preparing two conductive layers, each conductive layer comprising an array of conducting strips mounted upon a substrate arranged in a parallel orientation, wherein the conducting strips of the first conductive layer are oriented perpendicularly in relation to the conducting strips of the second conductive layer;
    (b) connecting at least two of the conducting strips to a communication line by:
        (i) placing a conducting plate across the conducting strips;
        (ii) applying an alternating potential to all conducting strips except one selected conducting strip; and
        (iii) measuring voltage between the selected strip and ground;
    (c) sandwiching a compressible layer between the two conductive layers; and
    (d) performing a pressure reading standardization test on the mat.

9. A method for manufacture of a pressure sensing mat, the method comprising the steps of:
    (a) preparing two conductive layers, each conductive layer comprising an array of conducting strips mounted upon a substrate arranged in a parallel orientation, wherein the conducting strips of the first conductive layer are oriented perpendicularly in relation to the conducting strips of the second conductive layer;
    (b) connecting at least two of the conducting strips to a communication line by:
        (i) placing a conducting plate across the conducting strips;
        (ii) applying an alternating potential to one selected conducting strip; and
        (iii) measuring voltage between all conducting strips except the selected strip and ground;
    (c) sandwiching a compressible layer between the two conductive layers; and
    (d) performing a pressure reading standardization test on the mat.

10. The method of claim 9, further comprising laminating the conducting plate with an insulating material.

11. A method for testing a pressure sensing mat comprising a first conductive layer comprising an array of parallel conducting strips, a compressible layer situated upon the first array and a second conductive layer comprising an array of parallel conducting strips situated upon the compressible layer, the conducting strips of each conductive layer being connected to a communication line, the method comprising the step of:
(a) for each conductive layer, measuring the resistance between at least one pair of adjacent conducting strips; and
(b) testing the electrical connection between each of the at least one pair of adjacent conducting strips and the communication line by:
  (i) placing a conducting plate across each pair of the conducting strips;
  (ii) applying an alternating potential to the conducting plate; and
  (iii) measuring voltage between each pair of the conducting strips and ground.

12. The method of claim 11, further comprising laminating each of the at least one pair of adjacent conductive strips with an insulating material.

13. The method of claim 11, wherein for step (a), each of the at least one pair of adjacent conductive strips is connected to a test monitor through a test probe.

14. The method of claim 11, wherein the at least one pair of adjacent conductive strips includes at least two pairs of adjacent conductive strips, and further comprising moving the test probe sequentially from one pair of adjacent conductive strips to the next until all the strips have been tested.

15. The method of claim 11 further comprising the step of:
(c) performing a pressure reading standardization test to said the pressure sensing mat.

16. The method of claim 15, wherein step (c) comprises the steps of:
  (i) exerting a known pressure upon at least one region of the pressure sensing mat;
  (ii) measuring pressure reading recorded by the pressure sensing mat; and
  (iii) comparing said the pressure reading with a look up table.

17. A method for testing a pressure sensing mat comprising a first conductive layer comprising an array of parallel conducting strips, a compressible layer situated upon the first array and a second conductive layer comprising an array of parallel conducting strips situated upon the compressible layer, the conducting strips of each conductive layer being connected to a communication line, the method comprising the step of:
(a) for each conductive layer, measuring the resistance between at least one pair of adjacent conducting strips; and
(b) testing the electrical connection between each of the at least one pair of adjacent conducting strips and the communication line by
  (i) placing a conducting plate across each pair of the conducting strips;
  (ii) applying an alternating potential to each pair of the conducting strips; and
  (iii) for each pair of the conducting strips measuring voltage between the conducting plate and ground.

18. A method for testing a pressure sensing mat comprising a first conductive layer comprising an array of parallel conducting strips, a compressible layer situated upon the first array and a second conductive layer comprising an array of parallel conducting strips situated upon the compressible layer, the conducting strips of each conductive layer being connected to a communication line, the method comprising the step of:
(a) for each conductive layer, measuring the resistance between at least one pair of adjacent conducting strips; and
(b) testing the electrical connection between each of the at least one pair of adjacent conducting strips and the communication line by
  (i) placing a conducting plate across each pair of the conducting strips;
  (ii) applying an alternating potential to all conducting strips except one selected conducting strip; and
  (iii) measuring voltage between the selected strip and ground.

19. A method for testing a pressure sensing mat comprising a first conductive layer comprising an array of parallel conducting strips, a compressible layer situated upon the first array and a second conductive layer comprising an array of parallel conducting strips situated upon the compressible layer, the conducting strips of each conductive layer being connected to a communication line, the method comprising the step of:
(a) for each conductive layer, measuring the resistance between at least one pair of adjacent conducting strips; and
(b) testing the electrical connection between each of the at least one pair of adjacent conducting strips and the communication line by
  (i) placing a conducting plate across each pair of the conducting strips;
  (ii) applying an alternating potential to one selected conducting strip; and
  (iii) measuring voltage between all conducting strips except the selected strip and ground.

* * * * *